(12) United States Patent
Moreton et al.

(10) Patent No.: US 7,456,136 B2
(45) Date of Patent: *Nov. 25, 2008

(54) LINEAR COMPOUNDS CONTAINING PHENOLIC AND SALICYLIC UNITS

(75) Inventors: David J. Moreton, Derbyshire (GB); Stephen J. Cook, Derbyshire (GB); David Cressey, Derbyshire (GB)

(73) Assignee: The Lubrizol Corporation, Wickliffe, OH (US)

( * ) Notice: Subject to any disclaimer, the term of this patent is extended or adjusted under 35 U.S.C. 154(b) by 644 days.

This patent is subject to a terminal disclaimer.

(21) Appl. No.: 10/487,192

(22) PCT Filed: Aug. 21, 2002

(86) PCT No.: PCT/US02/26592

§ 371 (c)(1),
(2), (4) Date: Feb. 19, 2004

(87) PCT Pub. No.: WO03/018728

PCT Pub. Date: Mar. 6, 2003

(65) Prior Publication Data

US 2004/0186027 A1    Sep. 23, 2004

Related U.S. Application Data

(60) Provisional application No. 60/314,825, filed on Aug. 24, 2001.

(51) Int. Cl.
*C10M 159/20* (2006.01)
*C10M 159/22* (2006.01)
*C07C 69/84* (2006.01)
*C07C 65/105* (2006.01)

(52) U.S. Cl. .................. 508/460; 508/186; 560/57; 560/66; 560/67; 560/70; 562/468; 562/476

(58) Field of Classification Search ............... 508/186, 508/460
See application file for complete search history.

(56) References Cited

U.S. PATENT DOCUMENTS 6,596,038 B1    7/2003  Moreton et al.
6,802,874 B2 *  10/2004 Moreton et al. ............ 44/389

FOREIGN PATENT DOCUMENTS

| EP | 0708171 A   | 4/1996 |
| EP | 0779355 A   | 6/1997 |
| WO | 99/25677 A1 | 5/1999 |
| WO | 99/25793 A1 | 5/1999 |
| WO | 02/072529 A1| 9/2002 |

* cited by examiner

*Primary Examiner*—Ellen M McAvoy
(74) *Attorney, Agent, or Firm*—Christopher D. Hilker; David M. Shold

(57) ABSTRACT

A linear compound and a metal salt or boron-containing metal salt thereof contains one or more carboxyl-containing phenol units or derivatives thereof and one or more on average at least $C_{18}$ hydrocarbyl-substituted hydroxyaromatic units or derivatives thereof connected by one or more divalent bridging groups. A concentrate contains the linear compound or metal salt thereof and an organic diluent. A lubricating oil composition contains a minor amount of the linear compound or metal salt thereof and a major amount of a lubricating oil. Additional embodiments of the invention are processes to make the linear compound and the metal salt thereof.

15 Claims, No Drawings

LINEAR COMPOUNDS CONTAINING PHENOLIC AND SALICYLIC UNITS

This application is a 371 of PCT/US02/26592 filed Aug. 21, 2002 which claims benefit of Ser. No. 60/314,825 filed Aug. 24, 2001.

FIELD OF THE INVENTION

This invention relates to linear compounds in the form of oligomers or polymers containing substituted phenol units and unsubstituted or substituted salicylic acid units. These compounds and metal salts of these compounds are useful as additives for lubricants.

BACKGROUND OF THE INVENTION

Lubricating oil compositions for gasoline fueled engines and diesel engines typically contain a variety of additives such as detergents and dispersants, antiwear agents, etc. Lubricating oils for medium- or low-speed diesel engines are known and will typically contain a range of additives which will perform a variety of functions: for example they may comprise dispersants to minimize deposit formation in various parts of the engine or detergent additives. However contamination of these lubricating oil compositions with unburned residual fuel oil is a problem recognized in the industry. This leads to severe engine cleanliness problems in service, which is sometimes referred to as "black paint." The problem is particularly widespread in 4-stroke trunk-piston engines where dirty cam boxes and crankcases are encountered. However, the problem is not confined to 4-stroke engines; 2-stroke crosshead engines can also suffer from the problem. These 2-stroke engines will usually use two separate lubricating oils, one for the crankcase and one for the cylinder, but it is in the crankcase where the heavy deposits potentially occur. It might be expected that the problem would be overcome simply by using more of the conventional dispersant additive in the lubricating oil, but this measure has met with very limited success.

Acidity in lubricating oil is another long-recognised problem. In the operation of the internal combustion engine by-products from the combustion chamber often blow by the piston and admix with the lubricating oil. Additives are generally employed to neutralise the acidic materials and disperse sludge within the lubricating oil. Examples are overbased alkaline earth metal sulfurized hydrocarbyl-substituted phenates, salicylates, naphthenates and sulfonates. The term "overbased" is generally used to describe those alkaline earth metal hydrocarbyl-substituted salts in which the ratio of the number of equivalents of the alkaline earth metal moiety to the number of equivalents of the acid moiety is greater than one. The ratio is usually greater than 1.2 and may be as high as 4.5 or greater. In contrast, the equivalent ratio of alkaline earth metal moiety to acid moiety in "normal" or "neutral" alkaline earth metal hydrocarbyl-substituted salts is one, and in "low-based" salts is less than one. The metal ratio is referred to herein by the term "MR." The overbased material usually contains greater than 20% in excess of the alkaline earth metal present in the corresponding neutral material. For this reason overbased alkaline earth metal hydrocarbyl-substituted salts have a greater capability for neutralising acidic matter than do the corresponding neutral alkaline earth metal hydrocarbyl-substituted salts, though not necessarily an increased detergency power. The degree of overbasing is expressed as "Total Base Number" or TBN, which is also sometimes referred to as Alkalinity Value or AV, and is measured by the method of ASTM Procedure D-2896.

International publications WO 99/25677 and WO 99/25793 disclose calixarenes containing within the calixarene ring at least one salicylic acid. The use of these compounds as fuel additives and lubricant additives is disclosed. Metal salts of these compounds as well as the use of such metal salts as lubricant additives are disclosed. These references indicate that in order to provide the calixarene ring structure it is necessary to use a reaction mixture containing at least 50% by weight solvent, preferably at least 80% by weight solvent, more preferably at least 90% by weight solvent. The references indicate that at solvent concentrations well below 50% by weight linear molecules are formed.

Copending U.S. patent application Ser. No. 09/802,500 filed Mar. 9, 2001, relates to linear phenol-salicylic acid condensation products used as lubricant and fuel additives.

European Patent Publication EP 0708171 A2 relates to lubricants containing metal salts, preferably overbased salts, of hydrocarbyl-substituted carboxyalkylene-linked phenols, dihydrocarbyl esters of alkylene dicarboxylic acids, the alkylene group being substituted with a hydroxy group and an additional carboxylic acid group, or alkylene-linked polyaromatic molecules, the aromatic moieties whereof comprise at least one hydrocarbyl-substituted phenol and at least one carboxy phenol, where the hydrocarbyl groups are of sufficient length to provide oil solubility to the salts and the salts exhibit good asphaltene suspension for marine diesel applications.

One object of this invention is to provide dispersant and detergent compositions for use in lubricating oil compositions.

Another object is to provide lubricating oil compositions with improved dispersancy performance, particularly with respect to reduction or elimination of "black paint" deposits.

It has now been found that considerably improved performance with respect to reduction or elimination of 'black paint' can be obtained with the compositions of this invention wherein the phenolic segments are substituted with hydrocarbyl groups containing on average at least 18 carbon atoms. It has also been observed that these provide excellent antioxidant properties. Moreover, we have also found that this effect is so marked that the phenolic sections may not have to be purely $C_{18}$ or greater substituted hydrocarbyl phenols, they can be mixtures of lower than $C_{18}$ and greater than C18 substituted hydrocarbyl phenols with no loss in anti-black paint performance, and possible economic advantages.

One of the main contributors to the sulfur and phosphorus level in a crankcase engine oil is the zinc dithiophosphate (ZDTP) antiwear agent. When the novel $C_{18-18+}$ alkylphenol-formaldehyde-salicylic acid resin compounds of this invention are overbased in the presence of boric acid so as to contain boron in the end overbased product, these are both good antiwear agents and detergents which can partially or fully replace ZDTP antiwear agents and sulfur-containing overbased detergents. The ZDTP antiwear agent level in the crankcase engine oil may be reduced, thus lowering the phosphorus and sulfur content of the crankcase engine oil. The sulfur level will be reduced further by the presence of sulfur free novel boron containing compound rather than traditional sulfur containing overbased detergents such as phenates and sulphonates.

SUMMARY OF THE INVENTION

This invention relates to a linear compound comprising m units of formula (I)

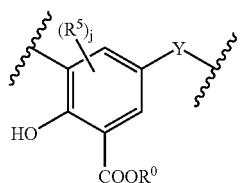

(I)

and n units of the formula (II)

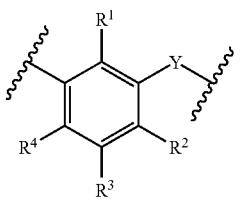

(II)

joined together, each end of the compound having a terminal unit which is independently hydrogen or one of the following formulae

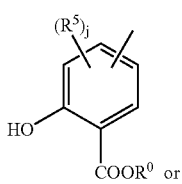

(III)

or

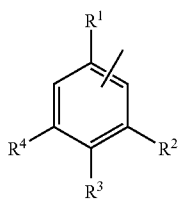

(IV)

wherein at least one of the terminal units is formula (III) or (IV); Y is a divalent bridging group which may be the same or different in each unit and that joins together units of formulae (I)-(IV); $R^0$ is hydrogen or a hydrocarbyl group, $R^5$ is hydrogen or a hydrocarbyl, j is 1 or 2; $R^3$ is hydrogen, a hydrocarbyl or a hetero-substituted hydrocarbyl group; either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl provided that at least one of $R^1$, $R^2$, $R^3$ and $R^4$ is hydrocarbyl containing on average at least 18 carbon atoms; m+n is at least 1; wherein on average the compound contains at least one unit of formula (I) or (III) and at least one unit of formula (II) or (IV); and the compound has a ratio of total number of units of formulae (I) and (III) to total number of units of formulae (II) and (IV) of about 0.1:1 to about 2:1. The invention further provides for metal salts of the foregoing compounds including boron-containing metal salts. The linear compounds and salts are useful as lubricant additives.

In engine oils for passenger cars and trucks there is pressure by original engine manufacturers to reduce the sulphur and phosphorus levels due to the possibility of sulphur and phosphorus compounds interfering with the functioning of exhaust emission treatment devices. The novel $C_{18}$ or greater alkylphenol-formaldehyde resin compounds which contain within the oligomer at least one salicylic acid unit are sulphur-free, so once overbased, will offer an advantage over more traditional sulphur containing overbased detergents such as phenates and sulphonates.

One of the main contributors to the sulphur and phosphorus level in a crankcase engine oil is the zinc dithiophosphate (ZDTP) antiwear agent. We have found that if the novel $C_{18}$ or greater alkylphenol-formaldehyde resin compounds which contain within the oligomer at least one salicylic acid unit are overbased in the presence of boric acid, so as to contain around 0.4% B in the end overbased product, these are good antiwear agents. This can allow the ZDTP antiwear agent level in the crankcase engine oil to be lowered, thus lowering the phosphorus and sulphur level of the crankcase engine oil. The sulphur level will be lowered still further by the presence of the sulphur-free novel boron-containing compound just described, rather than traditional sulphur containing overbased detergents such as phenates and sulphonates.

The inventive linear compounds, at least in one embodiment, are useful in the inventive lubricating oil compositions as surfactants and/or antioxidants. The metal salts, including the boron-containing metal salts, of the inventive linear compounds are useful in the inventive lubricating oil compositions, at least in one embodiment, as detergents or as both detergents and antiwear agents and in one embodiment, in reducing black paint in low- or medium-speed diesel engines.

DESCRIPTION OF THE PREFERRED EMBODIMENTS

The term "hydrocarbyl" denotes a group having a carbon atom directly attached to the remainder of the molecule and having a hydrocarbon or predominantly hydrocarbon character within the context of this invention. Such groups include the following:

(1) Purely hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc.

(2) Substituted hydrocarbon groups; that is, groups containing non-hydrocarbon substituents which do not alter the predominantly hydrocarbon character of the group. Those skilled in the art will be aware of suitable substituents. Examples include hydroxy, nitro, cyano, alkoxy, acyl, etc.

(3) Hetero groups; that is, groups which, while predominantly hydrocarbon in character, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

The terms "hydrocarbon" and "hydrocarbon-based" have the same meaning and can be used interchangeably with the term hydrocarbyl when referring to molecular groups having a carbon atom attached directly to the remainder of a molecule.

The term "lower" as used herein in conjunction with terms such as hydrocarbyl, alkyl, alkenyl, alkoxy, and the like, is intended to describe such groups that contain a total of up to 7 carbon atoms.

The term "oil-soluble" refers to a material that is soluble in mineral oil to the extent of at least about one gram per liter at 25° C.

The term "TBN" refers to total base number. This is the amount of acid (perchloric or hydrochloric) needed to neutralize all or part of a material's basicity, expressed as milligrams of KOH per gram of sample, measured by ASTM Procedure D-2896.

The Linear Compounds

The inventive linear compounds are in the form of linear oligomers or polymers containing units represented by the formulae (I), (II), (II) and (IV) depicted hereinabove. These compounds are comprised of units represented by formulae (I) and (II) connected to each other. At each end of the compound is a terminal unit which is independently hydrogen or one of the formulae represented by (III) or (IV) wherein at least one of the terminal units is formula (III) or (IV). The units represented by formulae (I) and (II) may be distributed in random or block patterns. Preferably, the compound contains on average at least one unit represented by formulae (I) or (III) and at least one unit represented by formulae (II) or (IV). For example, the linear compounds may include one or more block of units corresponding to -(II)(II)-, -(II)(II)(II)-, -(II)(II)(II)(II)-, etc.

Examples of the inventive compounds include the following (III)-(IV)
(III)-(II)-(IV)
(III)-(II)-(II)-(II)-(I)-(II)-(III)
(III)-(II)-(I)-(I)-(II)-(II)-(II)-(IV)
(IV)-(I)-(I)-(II)-(II)-(II)-(I)-(III)
(III)-(II)-(II)-(I)-(II)-(II)-(III)
(IV)-(I)-(II)-(II)-(II)-(II)-(II)-(IV)
(III)(II)(II)(II)(II)(II)(II)(I)(II)(II)(II)(IV)
(IV)((II))$_{10}$(I)((II))$_5$(I)(I)((II))$_8$(I)(IV)
(III)((I))$_5$(II)((I))$_{10}$(II)(II)(II)(IV)
(IV)((II))$_{20}$(I)((II))$_{10}$(I)(IV)
(IV)((II))$_{40}$(I)(I)(II)$_5$(IV)

The total number of units represented by formula (I) in the inventive linear compound is m, and the total number of units represented by formula (II) is n. In one embodiment m is at least 1 and n is at least 2. The total of m+n is at least 2, preferably at least 3, and in one embodiment at least about 4, and in one embodiment at least about 5, and in one embodiment at least about 6, and in one embodiment at least about 7, and in one embodiment at least about 8. The total of m+n may range from 2, often from about 3 to about 50, and in one embodiment about 4 to about 50, and in one embodiment about 5 to about 50, and in one embodiment about 6 to about 50, and in one embodiment about 7 to about 50, and in one embodiment about 8 to about 50, and in one embodiment 3 to about 40, and in one embodiment 3 to about 30, and in one embodiment 3 to about 20. The ratio of m to n ranges from about 0.1:1 to about 2:1, and in one embodiment about 0.1:1 to about 1:1, and in one embodiment about 0.1:1 to about 0.5:1, and in one embodiment 0.1:1 to about 0.3:1, and in one embodiment about 0.1 4-0.15:1.

In formulae (I) and (II), each Y is a divalent bridging group that joins together the units of formulae (I)-(IV) and that may independently be represented by the formula $(CHR^6)_d$ in which $R^6$ is either hydrogen or hydrocarbyl and d is an integer which is at least 1. In one embodiment, $R^6$ contains 1 to about 6 carbon atoms, and in one embodiment 1 or 2 carbon atoms, and in one embodiment it is methyl. In one embodiment, d is from 1 to about 4. Y may optionally be sulfur rather than $(CHR_6)_d$ in up to 50% of the units, such that the amount of sulfur incorporated in the molecule is up to 50 mole %. In one embodiment, the amount of sulfur is between 8 and 20 mole %, and in one embodiment the compound is sulfur-free.

In formulae (I) and (III), $R^0$ is hydrogen or a hydrocarbyl (e.g., alkyl) group of 1 to about 6 carbon atoms, and in one embodiment 1 or 2 carbon atoms. $R^5$ is hydrogen or a hydrocarbyl group of 1 to about 10 carbon atoms, and in one embodiment 1 to about 6 carbon atoms, and in one embodiment 1 to about 3 carbon atoms, and in one embodiment 1 to about 8 carbon atoms, and in one embodiment 1 to about 2 carbon atoms.

In formulae (II) and (IV), $R^3$ is hydrogen or a hydrocarbyl of 1 to about 200 carbon atoms, and in one embodiment 1 to about 100 carbon atoms, and in one embodiment 1 to about 60 carbon atoms, and in one embodiment 1 to about 30 carbon atoms, and in one embodiment 1 to about 18 carbon atoms, in one embodiment about 12 carbon atoms, and in one embodiment on average at least 18 carbon atoms. $R^3$ may be dodecyl or derived from propylene tetramer. $R^3$ may be hetero-substituted. The hetero atoms or groups may be —O— or —NH—. In one embodiment, $R^3$ is an alkoxyalkyl group; either $R^1$ is hydroxyl and $R^2$ and $R^4$ are independently either hydrogen, hydrocarbyl or hetero-substituted hydrocarbyl, or $R^2$ and $R^4$ are hydroxyl, and $R^1$ is either hydrogen, hydrocarbyl or hetero-substituted hydrocarbyl. The hydrocarbyl and hetero-substituted hydrocarbyl groups independently contain 1 to about 200 carbon atoms, and in one embodiment 1 to about 100 carbon atoms, and in one embodiment 1 to about 60 carbon atoms, and in one embodiment 1 to about 30 carbon atoms, and in one embodiment 1 to about 18 carbon atoms, and in one embodiment 1 to about 12 carbon atoms, and in one embodiment 1 to about 6 carbon atoms. The hetero substituents may be —O— or —NH—, provided that at least one of $R^1$, $R^2$, $R^3$ and $R^4$ is hydrocarbyl containing on average at least 18 carbon atoms and preferably at least 30 carbon atoms.

In one embodiment, Y is $CH_2$; $R^1$ is hydroxyl; $R^2$ and $R^4$ are hydrogen; $R^3$ is a hydrocarbyl group of about 18 to about 200 carbon atoms, often to about 60 carbon atoms, and in one embodiment about 18 to about 45 carbon atoms, and in one embodiment about 18 to about 30 carbon atoms, and in one embodiment from about 30, often from about 40 to about 100 carbon atoms, and in one embodiment about 30 to about 60 carbon atoms; $R^0$ is hydrogen; $R^5$ is hydrogen; j is 1; and m+n has a value of at least 1, and in one embodiment at least 2, and in one embodiment at least about 3; and m is 0, 1 or 2, and in one embodiment m is 1.

In one embodiment, either or both of the terminal groups represented by the formulae (III) and (IV) has a —$CH_2OH$ group attached to the aromatic ring in an ortho position relative to the hydroxyl group.

In an embodiment of the present invention the linear compound contains one or more units of formulae (II) and (IV) wherein a portion of said units have a $R^3$ hydrocarbyl group containing about 8 to about 20 carbon atoms and a remaining portion of said units having a $R^3$ hydrocarbyl group containing about 21 to about 45 carbon atoms where the $R^3$ hydrocarbyl groups from the said portions on average contain at least 18 carbon atoms. This linear compound having $R^3$ groups containing on average at least 18 carbon atoms can be prepared in several ways. The compound can be prepared from a mixture of starting units of formulae (II) and (IV) having $R^3$ groups with different numbers of carbon atoms such as $C_{12}$ and $C_{40}R^3$ groups. The compound can also be prepared by mixing two or more compounds where each of these compounds is prepared from units of formulae (II) and (IV) having a $R^3$ group with a given number of carbon atoms; e.g., the compound is prepared by mixing compound 1 and compound 2 where compound 1 contains $C_{12}R^3$ groups and compound 2 contains $C_{40}R^3$ groups.

The process for making the inventive linear compounds comprises reacting together optionally in an organic solvent, in the presence of a basic catalyst, compounds of the formulas (Ia) and (IIa)

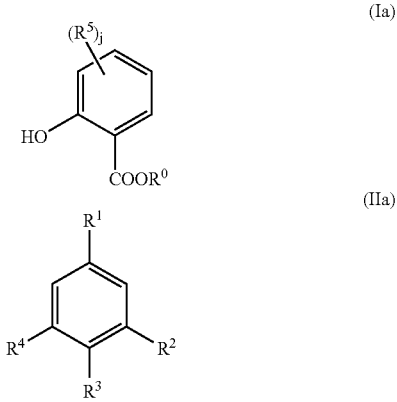

with an aldehyde of the formula $O=CHR^6$, and optionally sulfur; where $R^0$ to $R^6$ and j are as defined previously.

The formaldehyde may be paraformaldehyde, an aqueous solution of aldehyde (formalin), or a solution of an aldehyde in methanol.

The basic catalyst may be an alkali or alkaline earth metal hydroxide such as sodium hydroxide, potassium hydroxide, and the like; ammonia; or a hindered amine. The hindered amines that are useful include tetra alkyl ammonium hydroxides such as tetra methyl ammonium hydroxide, tetrabutyl ammonium hydroxide, and the like, as well as the trialkyl monoamines such as triethyl amine, and the like. The molar ratio of the basic catalyst to the number of moles of compound represented by formula (IIa) may range from about 0.005:1 to about 0.5:1, and in one embodiment about 0.02:1 to about 0.3:1, and in one embodiment about 0.02-0.04:1.

Alternatively, the basic catalyst may be a basic ion exchange resin such as the AMBERLITE® resins provided by Rohm & Haas or the DOWEX® resins provided by Dow. These are macroreticular resins which are strongly basic in nature and have moderate porosities. Specific resins that may be used include Amberlite IRA 410 and Dowex 550 OH. These resins may be used at a concentration of about 0.1 to about 30% by weight based on the overall weight of the reaction mixture, and in one embodiment about 0.1 to about 10% by weight.

As noted hereinabove, the reaction of this invention may be conducted in the presence of an organic solvent such as toluene, a mineral oil, or a mixture thereof. Frequently, the concentration of organic solvent (if used) in the reaction mixture is up to about 48% by weight of the reaction mixture, and in one embodiment from about 5% to about 48% by weight, and in one embodiment about 15% to about 48% by weight, and in one embodiment about 30% to about 48% by weight of the reaction mixture. In one embodiment, the solvent comprises about 32% to about 46% by weight of the reaction mixture, and in one embodiment about 35% to about 45% by weight.

The reactants corresponding to (Ia) and (IIa) may be combined with the aldehyde simultaneously or stepwise.

In one preferred embodiment, the compounds corresponding to formula (IIa) are permitted to oligomerize, at least partially, before adding the compounds corresponding to formula (Ia) to the reaction mixture. Thus, in this embodiment of the inventive process, the compound corresponding to formula (IIa) is mixed with the solvent (if used) and reacted with the aldehyde in the presence of the basic catalyst prior to the addition of the compound corresponding to formula (Ia). As a result, the inventive linear compounds of this embodiment will contain at least one block of one or more units corresponding to formula (IIa) linked to each other. For example, the inventive linear compounds may have one or more blocks of units corresponding to -(IIa)-(IIa)(IIa)-, -(IIa)(IIa)(IIa)-, -(IIa)(IIa)(IIa)(IIa)-, etc.

Metal Salts of the Linear Compounds

In one embodiment of the invention, low based, neutral or overbased salts of the inventive linear compounds are provided. The process for making the low-based or neutral salts comprises the steps of: (I) forming a mixture of components (A) and (C); and (II) adding a metal base (B) to the mixture of components (A) and (C), the addition of the metal base (B) to the mixture of (A) and (C) being in a single addition or in a plurality of additions, steps (I) and (II) being performed concurrently or sequentially.

Component (A) may be either (i) the inventive linear compound having at least one substituent hydroxyl group available for reaction with a metal base, or (ii) a low-based or neutral metal salt of the inventive linear compound having at least one substituent hydroxyl group available for reaction with the metal base.

Component (B) is a metal base. The metal moiety may be an alkali or alkaline earth metal, and in one embodiment an alkaline earth metal. The metal may be calcium, magnesium or barium, and in one embodiment it is calcium. The base moiety may be an oxide or a hydroxide. A calcium base may be added, for example, in the form of quick lime (CaO) or in the form of slaked lime (Ca(OH)$_2$) or mixtures of the two in any proportion. Component (B) may be added in whole to the initial reactants or in part to the initial reactants and the remainder in one or more further additions at intermediate points during the reaction.

Component (C) is solvent comprising either component (C-1) or (C-2). Component (C-1) is either (i) a polyhydric alcohol having about 2 to about 4 carbon atoms, (ii) a di-(C$_3$ or C$_4$)glycol, (iii) a tri-(C$_2$-C$_4$)glycol or (iv) a mono- or polyalkylene glycol alkyl ether of the formula:

$$R^1(OR^2)_fOR^3 \tag{V}$$

wherein in the formula (V), $R^1$ is an alkyl group of 1 to about 6 carbon atoms, $R^2$ is an alkylene group of 1 to about 6 carbon atoms; $R^3$ is hydrogen or an alkyl group of 1 to about 8 carbon atoms, and f is an integer from 1 to about 6. Examples include the monomethyl or dimethyl ethers of ethylene glycol, diethylene glycol, triethylene glycol or tetraethylene glycol. A useful compound is methyl diglycol. Mixtures of glycol ethers and glycols may be used. The polyhydric alcohol may be either a dihydric alcohol, for example ethylene glycol or propylene glycol, or a trihydric alcohol, for example glycerol. The di-($C_3$ or $C_4$)glycol may be dipropylene glycol, and the tri-($C_2$ to $C_4$)glycol may be triethylene glycol.

In one embodiment, component (C-1) further comprises: (a) a hydrocarbon solvent; or (b) either (i) water, (ii) a monohydric alcohol of 1 to about 20 carbon atoms, (iii) a ketone having up to 20 carbon atoms, (iv) a carboxylic ester having up to 10 carbon atoms, (v) an aliphatic, alicyclic or aromatic ether having up to 20 carbon atoms, or a mixture of two or more of (i) to (v). Examples include methanol, 2-ethyl hexanol, cyclohexanol, cyclohexanone, benzyl alcohol, ethyl acetate and acetophenone.

Component (C-2) is a monohydric alcohol of 1 to about 4 carbon atoms in combination with a hydrocarbon solvent.

The hydrocarbon solvent may be aliphatic or aromatic. Examples of suitable hydrocarbon solvents include toluene, xylene, naphtha and aliphatic paraffins, for example hexane, and cycloaliphatic paraffins.

In one embodiment, it is useful to incorporate an oil of lubricating viscosity as a supplemental solvent. The oil may be an animal, vegetable or mineral oil. The oil may be a petroleum derived lubricating oil, such as a naphthenic base, paraffin base or mixed base oil. Solvent neutral oils may be used. The oil may be a synthetic oil. Suitable synthetic oils include synthetic ester oils, which oils include diesters such as di-octyl adipate, di-octyl sebacate and tri-decyladipate, or polymeric hydrocarbon oils, for example liquid polyisobutenes and poly-alpha olefins.

Useful solvents (C) include ethylene glycol, a mixture of ethylene glycol and 2-ethyl hexanol, and a mixture of methanol and toluene.

In one embodiment, the invention includes a process for the production of overbased metal salts of the inventive linear compounds which comprises the foregoing process for making a low based or neutral metal salt of the inventive linear compound but with the addition of the following step: (III) adding (D) carbon dioxide to the mixture of components (A), (B) and (C) subsequent to each addition of component (B). The carbon dioxide may be added in the form of a gas or a solid, preferably in the form of a gas. In gaseous form it may be blown through the reaction mixture.

The weight ratio of component (A) to component (C) may be from about 10 to about 65 parts by weight of (A) per 100 parts by weight of (C), and in one embodiment about 20 to about 60 parts by weight of (A) per 100 parts by weight of (C). The ratio of mole equivalents of component (B) to mole equivalents of component (A) may be from about 0.05 to about 20 mole equivalents of (B) per mole equivalent of (A), and in one embodiment about 0.08 to about 18 mole equivalents of (B) per mole equivalent of (A). The ratio of the number of moles of metal in component (B) to the number of moles of carbon dioxide in (D) may be from about 0.3 to about 1.6 moles of metal in (B) per mole of carbon dioxide in (D), and in one embodiment about 0.55 to about 1.3 moles of metal in (B) per mole of carbon dioxide in (D).

In one embodiment, the reaction mixture may include component (E). Component (E) is either (i) a carboxylic acid containing from about 6 to about 100 carbon atoms or an anhydride thereof, (ii) a di- or polycarboxylic acid containing from about 36 to about 100 carbon atoms or an anhydride thereof, (iii) a hydrocarbyl-substituted sulphonic acid or an anhydride thereof, (iv) a hydrocarbyl-substituted salicylic acid or an anhydride thereof, (v) a hydrocarbyl-substituted naphthenic acid or an anhydride thereof, (vi) a hydrocarbyl-substituted phenol or (vii) a mixture of any two of (i) to (vi). Component (E) may be added during step (I), (II) or (III), or prior to or subsequent to any of the foregoing steps. In one embodiment, component (E) is added during step (I). When component (E) is used, it may be used in an amount of up to about 40% by weight based on the combined weight of components (A), (B), (C), (D) and (E), and one embodiment from about 2 to about 38% by weight, and in one embodiment from about 12 to about 27% by weight.

Component (i) of component (E) may be an acid having the formula:

(VI)

wherein in formula (VI), $R^1$ is an alkyl or alkenyl group of about 10 to about 24 carbon atoms, and $R^2$ is either hydrogen, an alkyl group of 1 to about 4 carbon atoms or a —$CH_2COOH$ group. $R^1$ may be an unbranched alkyl or alkenyl group. Examples of the saturated acids that may be used include capric, lauric, myristic, palmitic, stearic, isostearic, arachidic, behenic and lignoceric acids. Examples of the unsaturated acids that may be used include lauroleic, myristoleic, palmitoleic, oleic, gadoleic, erucic, ricinoleic, linoleic and linolenic acids. Mixtures of any of the foregoing acids may also be employed, for example, ripe top fatty acids. Suitable mixtures of acids are those commercial grades containing a range of acids, including both saturated and unsaturated acids. Such mixtures may be obtained synthetically or may be derived from natural products, for example, tall, cotton, ground nut, coconut, linseed, palm kernel, olive, palm, castor, soybean, sunflower, herring and sardine oils and tallow. In one embodiment, component (i) of component (E) is an acid anhydride, acid chloride or ester derivative of any of the foregoing acids.

Component (ii) of component (E) may be a polyisobutylene substituted succinic acid or a polyisobutylene substituted succinic anhydride. The molecular weight of such acid or anhydride may be in the range of about 300 to about 3000, and in one embodiment about 700 to about 1300.

As regards to components (iii), (iv), (v) and (vi) of component (E), the hydrocarbyl substituent may contain up to about 125 aliphatic carbon atoms, and in one embodiment about 6 to about 20 carbon atoms. Examples of suitable substituents include alkyl groups, for example hexyl, cyclohexyl, octyl, isooctyl, decyl, tridecyl, hexadecyl, eicosyl and tricosyl. Hydrocarbyl groups derived from the polymerization of both terminal and internal olefins, for example ethene, propene, 1-butene, isobutene, 1-hexene, 1-octene, 2-butene, 2-pentene, 3-pentene and 4-octene may be used. In one embodiment, the hydrocarbyl substituent is derived from polypropylene, poly-1-butene or polyisobutylene.

The reaction mixture may also include as component (F) a catalyst (or promoter) for the reaction. The catalyst may be an organic compound or an inorganic compound. The catalyst (F) is added during step (I), (II) or (III), or prior to or subsequent to any of the foregoing steps. In one embodiment, the catalyst (F) is added during step (I). When component (F) is used, the amount of component (F), added to the mixture of (A), (B), (C), (D) and optionally (E) ranges from about 0.1% to about 3% by weight based on the combined weight of the mixture, and in one embodiment about 2% by weight. Suitable organic compounds include (i) organic halides (e.g., chlorides, bromides, iodides) or (ii) organic alkanoates, which may be represented by the formula:

R—X (VII)

wherein in formula (VII), R is either an alkyl, aryl or alkaryl group which may have about 3 to about 20 carbon atoms, about 6 to about 20 carbon atoms, or about 7 to about 20 carbon atoms, respectively, or a halo-derivative thereof. X is either halogen, suitably chlorine, bromine or iodine, preferably chlorine, or the group $OCOR^1$ wherein $R^1$ is an alkyl group of 1 to about 4 carbon atoms. Alternatively, the organic halide may be an HX salt of an organic base, for example guanidine hydrochloride. An example of an organic halide represented by formula (VII) is octyl chloride. Mixtures of (i) and (ii) of component (F) may be employed. Suitable inorganic compound catalysts include inorganic halides, particularly inorganic chlorides, and inorganic alkanoates. Examples of suitable inorganic compound catalysts include calcium acetate, calcium chloride, ammonium chloride, ammonium acetate, aluminum chloride and zinc chloride. Provided that the catalyst is present during the carbonation step (i.e., step (III)), it may be added at any point in the process, though it is usually convenient to add the catalyst initially during step (I).

In order to produce an overbased salt from component (A)(i) or (A)(ii) it is necessary to react component (A) with components (B), (C) and (D), using the appropriate proportions of components (A) and (B) to achieve overbasing. Suitably component (B) may be added in one or more additions.

In order to produce a high TBN overbased metal salt of the inventive linear compound there may be employed an overbased metal salt of the inventive linear compound derived from one of the inventive linear compounds having a substituent group or groups available for reaction, and it is preferred to employ component (E), particularly either (E)(i) or (ii), and more particularly stearic acid, while at the same time adjusting the relative amounts of components (A) and (B) to a value sufficient to produce the desired high TBN metal salt.

The temperature at which the process is operated may be a temperature in the range from about 15 to about 200° C., and in one embodiment from about 50 to about 175° C. The selection of the optimum temperature within the aforesaid range is dependent in part on the nature of the solvent employed.

Generally, the process is operated in the presence of a lubricating oil. At the conclusion of the process it is preferred to recover the salt as a solution in lubricating oil by separating off volatile fractions, for example, by distillation at subatmospheric pressure. Finally, it is preferred to filter the solution. Alternatively, the solution may be centrifuged.

Salts produced by the above process may have TBNs of 60 mg KOH/g or below, (i.e., low based or neutral metal salt of the inventive linear compounds). In one embodiment, these have TBN ranging from about 10 to 60, often to about 40 and in one embodiment, to about 30. In one embodiment, the salts are overbased, in which case they generally have TBNs of greater than 60 mg KOH/g, often at least about 100 mg KOH/g, in one embodiment at least about 200 mg KOH/g, and in one embodiment from about 200 up to about 500 mg KOH/g, and in one embodiment from about 300 up to about 500 mg KOH/g, and in one embodiment from about 350 up to about 500 mg KOH/g, and in one embodiment from about 400 up to about 500 mg KOH/g.

In an embodiment of the present invention overbased metal salts of the linear compound, having a TBN ranging from about 60 to about 500 mg KOH/g or from about 100 to about 500 mg KOH/g, can contain boron. The boron-containing overbased metal salts can be prepared by adding a borating agent, such as boric acid or the alcohol borate tributyl borate, any time during or after the preparation of the overbased metal salts of the linear compound. In one instance the borating agent is added at the very beginning of the overbasing process. In another instance the borating agent is added to the overbased metal salt of the linear compound, and the mixture is then heated to temperatures of about 100 to about 200° C. sometimes under reduced pressure and/or in presence of a solvent such as xylenes or toluene to facilitate removal of volatile reaction products such as water or alcohols.

The salts including boron-containing salts may be supplied in the form of a concentrate. These concentrates are comprised of the foregoing salt and a substantially inert, normally liquid organic diluent such as mineral oil, synthetic oil (e.g., ester of dicarboxylic acid), naphtha, alkylated (e.g., $C_{10}$-$C_{13}$ alkyl) benzene, toluene or xylene to form an additive concentrate. These concentrates usually contain from about 1% to about 99% by weight, and in one embodiment about 10% to about 90% by weight of the diluent.

Lubricating Oil Compositions

The inventive lubricating oil compositions are based on diverse oils of lubricating viscosity, including natural and synthetic lubricating oils and mixtures thereof. The lubricating oil compositions may be lubricating oils useful in industrial applications and in automotive engines, transmissions and axles. These lubricating oil compositions are effective in a variety of applications including crankcase lubricating oils for spark-ignited and compression-ignited internal combustion engines, including automobile and truck engines, two-cycle engines, aviation piston engines, marine and low-load diesel engines, and the like.

In one embodiment, the inventive lubricating oil composition is suitable for use in either low- or medium-speed engines, especially marine diesel engines. Typically such engines are 4-stroke trunk piston engines having an engine speed of 300-2,000 rpm, and in one embodiment 400-800 rpm, and a brake horse-power (BHP) per cylinder of 10-3,000, and in one embodiment 150-1,900. The engine can also be a 2-stroke cross-head engine having a speed of 50-350 rpm, and in one embodiment 100-250 rpm and a BHP per cylinder of 500-7,500.

The lubricating oil compositions employ an oil of lubricating viscosity that is generally present in a major amount (i.e. an amount greater than about 50% by weight). In one embodiment, the oil of lubricating viscosity is present in an amount greater than about 60% by weight, or greater than about 70% by weight, or greater than about 80% by weight.

In one embodiment, the oil of lubricating viscosity is selected to provide a lubricating composition of at least an SAE gear oil viscosity number of about 60 or about 65. The lubricating composition may also have a so-called multigrade rating such as SAE 60W-80, 65W-80, 65W-90, 75W-80, 75W-90, 80W-90, 80W-140 or 85W-140. Multigrade lubricants may include a minor viscosity improving amount of a viscosity improver which is formulated with the oil of lubricating viscosity to provide the above lubricant grades. Useful viscosity improvers include polyolefins, styrene-diene polymers and polymethacrylates.

In one embodiment, the oil of lubricating viscosity is selected to provide lubricating compositions with crankcase applications such as for gasoline and diesel engines. Typically, the lubricating compositions are selected to provide an SAE crankcase viscosity number of 10W, 20W or 30W grade lubricants. The lubricating compositions may also have a so-called multi-grade rating such as SAE 10W-30, 10W-40, 10W-50, etc. As described above, the multi-grade lubricants include a viscosity improver which is formulated with the oil of lubricating viscosity to provide the above lubricant grades.

Oils of lubricating viscosity generally include natural oils, synthetic oils, and mixtures thereof. Natural oils include animal and vegetable oils such as lard oil and soybean oil, and mineral oils derived from various sources such as petroleum crudes, coal and shale. Synthetic oils include olefin homopolymers and copolymers such as poly(alpha-olefins) and ethylene-propylene copolymers, carboxylic acid esters such as bisesters of dicarboxylic acids, and polyalkylene glycols to include ether and ester derivatives thereof. Specific examples of the above-described oils of lubricating viscosity are given in Chamberlin, III., U.S. Pat. No. 4,326,972, European Patent Publication 107,282, and A. Sequeria, Jr., Lubricant Base Oil and Wax Processing, Chapter 6, Marcel Decker, Inc., New York (1994), each of which is hereby incorporated by reference for relevant disclosures contained therein. A basic, brief description of lubricant base oils appears in an article by D. V. Brock, "Lubrication Engineering", Volume 43, pages 184-5, March, 1987, which article is expressly incorporated by reference for relevant disclosures contained therein.

The lubricating oil compositions of the present invention may have a TBN in the range from about 0.1 to about 100 mg KOH/g. When the composition is to be used in a 4-stroke trunk piston engine the TBN may be in the range from about 5 to about 70, and in one embodiment about 8 to about 50 mg KOH/g. When it is to be used in a 2-stroke cross-head engine and particularly for the crankcase, the TBN of the composition may be in the range from about 0.1 to about 15, and in one embodiment in the range from about 1 to about 10 mg KOH/g.

The inventive lubricating oil composition may be contaminated with a fuel oil which has a residual oil content. These fuel oils are suitable for use as diesel fuel oils. Fuel oils can in general be divided into two main categories, namely, distillates and heavy fuels. Distillates consist of one or more distilled fractions. Heavy fuels are fuels that comprise at least a proportion of a residual oil; that is, an oil that remains after the distilled fractions have been removed from an unrefined oil. The composition of the residual oil will vary with the composition of the starting oil which is usually a crude oil and will also vary depending upon the distillation conditions. However, by its nature residual oil is of high molecular weight and high boiling point. Heavy fuels can also comprise, in addition to residual oil, distillates. However, heavy fuels generally comprise at least about 90% by weight, and in one embodiment at least about 95% by weight, and in one embodiment at least about 99% by weight residual oil. In one embodiment, the present invention relates to lubricating oil compositions that are contaminated with a heavy fuel. The amount of heavy fuel in the lubricating oil composition will vary. The lubricating oil composition may contain between about 0.1 to about 25% by weight, and in one embodiment about 0.1 to about 10% by weight, and in one embodiment about 0.3 to about 5% by weight, and in one embodiment, about 0.5 to about 3% by weight heavy fuel oil, which as defined above is a fuel oil which has a residual oil content. The use of these contaminated lubricating oil compositions in low- or medium-speed diesel engines such as 4-stroke piston engines and 2-stroke cross-head engines can lead to an engine cleanliness problem known as "black paint." By including the inventive linear compounds or metal salts thereof in these contaminated lubricating oil compositions the problem of black paint may be reduced or eliminated. Overbased metal salts of these compounds also function as high TBN detergents, thereby providing two functions in one product.

In addition to the lubricating oil and the inventive linear compound or metal salt or boron-containing metal salt thereof, the inventive lubricating oil compositions may contain other additives known in the art. These include dispersants. Although any type of dispersant may be employed in the composition, a suitable dispersant is one derived from a hydrocarbyl-substituted succinic acid or anhydride by reaction with an amine, i.e. a hydrocarbyl-substituted succinimide such as a polyisobutylene-substituted succinimide. These succinimides are well known in the art. Succinimide production is described in, for example, the following U.S. Pat. Nos.: 2,992,708; 3,018,291; 3,024,237; 3,100,673; 3,219,666; 3,172,892; 3,272,746; 4,234,435; 4,904,410 and 6,165,235. Succinimide dispersants that are mono- or bis-succinimides may be employed.

In addition to the foregoing, the inventive lubricating oil composition may contain one or more additives conventionally employed in lubricating oil compositions. Examples of such additives include additional detergents, foam inhibitors, extreme pressure/antiwear agents, rust inhibitors, antioxidants, and the like. The additional detergents that can be employed include hydrocarbyl-substituted alkaline earth metal phenates, salicylates, naphthenates, sulphonates or carboxylates, which may be neutral or overbased materials. The concentration of each of these when used may range from about 0.001% to about 20% by weight.

The lubricating oil composition of the present invention can be prepared by mixing a concentrate comprising an organic diluent and a linear compound or metal salt thereof of this invention, optionally a suitable diluent such as a hydrocarbon solvent or mineral oil, and optionally other useful additives described hereinabove with the oil of lubricating viscosity until the mixture is homogeneous.

In one embodiment, the inventive lubricating oil composition contains a detergency-improving and black paint-reducing amount of the inventive linear compound or metal salt thereof of about 0.01 to about 10% by weight of the inventive linear compound or metal salt thereof based on the weight of the lubricating oil composition, in one embodiment about 0.01 to about 7% by weight, in one embodiment about 0.01 to about 5% by weight, in one embodiment about 0.05 to about 4% by weight, and in one embodiment about 0.1 to 3% by weight.

As indicated above, the inventive linear compounds or metal salts thereof may be used for reducing black paint in low- or medium-speed diesel engines. The lubricating compositions used for these applications may comprise up to about 5% to about 10% by weight, and in one embodiment from about 0.1% to about 3% by weight of a hydrocarbyl-substituted succinimide dispersant; from about 0.05 to about 5% by weight, and in one embodiment from about 0.1% to about 3% of a inventive linear compound or metal salt thereof; and a low-or medium-speed diesel engine lubricating oil.

The following examples illustrate compositions of this invention. All temperatures are in degrees Celsius (° C.), parts and percentages are by weight. Filtrations are conducted with a diatomaceous earth filter aid. SN150 oil is a 150 neutral oil obtained from Exxon.

EXAMPLE 1

A 2 L flange flask is charged with 346 g dodecylphenol (propylene tetramer derived, 1.32 moles, 1 equivalent (eq)); 95.6 g salicylic acid (0.69 mole, 0.52 eq); 226.9 g of 36.7% by weight formaldehyde in water (formalin) (1.70 moles, 1.356 eq); 45 g 25% aqueous ammonia (0.65 mole, 0.5 eq), and 500 g toluene (solvent). A reaction apparatus is set up using the flask, a flange lid and clip, overhead stirrer with paddle and polytetrafluoroethylene (PTFE) stirrer gland, Dean Stark trap and double surface condenser, an electric mantle/thermocouple/Eurotherm temperature controller system, the glassware from just above the mantle to just below the condenser being covered with glass wool. The reactor contents are heated with stirring to 85° C. and are held for 1.5 hours. The temperature is increased to 105° C., and maintained for 3 hours while collecting 229 g water via the Dean & Stark trap. The temperature is increased to 120° C. and is maintained for 1.5 hours with refluxing toluene. The toluene is removed on a rotary evaporator at 100° C. and 75 mm Hg then mixed with sufficient mineral oil (SN150) to provide a 50% solution. The solution is the product. Yield=1011 g, 100%. Mass spec indicates that the product consists of a mixture of linear compounds containing units derived from both dodecyl phenol and salicylic acid, a majority of which is 2 dodecylphenol molecules and 1 salicylic acid molecule methylene bridged together.

EXAMPLES 2-4 as indicated below were prepared following the procedure of Example 1:

Example 2—1 equiv of $C_{18}$ phenol coupled with 1.3 equiv of salicylic acid,
Example 3—1 equiv of $C_{18}$ phenol coupled with 0.5 equiv of salicylic acid, and
Example 4—1 equiv of polyisobutyl (550 mol. wt.) phenol coupled with 1 equiv of salicylic acid.

EXAMPLE 5

The apparatus used in Example 1 is used. The flask is charged with 475 g polyisobutenyl ($\overline{M}_n$ 550, derived from GLISSOPAL® 550 (BASF)) substituted phenol (0.739 mole, 1 eq) and 330 g mineral oil (SN150) and heated to 30° C. Via a pressure equalizing dropping funnel, 3.4 g of 50% aqueous KOH (0.030 mole, 0.04 eq) are added all at once. The materials are heated to 75° C. followed by addition over 0.5 hour via a pressure equalizing dropping funnel, 81.6 g 37% aqueous formaldehyde (formalin) (1.01 moles, 1.367 eq) followed by heating at 75° C. for 2 hours until free formaldehyde measures less than 2% (by titration). To the reaction are charged 51.6 g salicylic acid (0.374 mole, 0.51 eq) and the reaction is heated to 140° C. as quickly as possible (0.3 hour) while controlling reflux, draining water of reaction via a Dean Stark trap. The reaction is held at 140° C. for 1.5 hours while collecting 58 ml water. The materials are vacuum stripped at 140° C./100 mm Hg over 0.5 hour. The clear and golden residue is the product. Yield=857 g, % K=0.093%. Mass spec, GPC and $H^1$ and $C^{13}$ NMR indicate that the product consists of 2 methylene bridged polyisobutenyl phenol molecules methylene bridged to one salicylic acid.

Example 6 was a repeat of Example 5 on a larger scale.

EXAMPLE 7

A 2-liter flask is charged with 250 g (0.58 mole, 1 eq) of the dodecylphenol-salicylic acid resin of Example 1, 30 g dodecylphenol (propylene tetramer derived) (0.115 mole, 0.12 eq), 125 g tall oil fatty acid (0.442 mole, 0.76 eq), 15 g (0.24 mole, 0.4 eq) ethylene glycol, 90 g (1.22 mole, 2.1 eq) Ca(OH)$_2$, 40 g mineral oil (SN150) and 260 g 2-ethylhexanol (solvent). The materials are heated and stirred under vacuum (480 mm Hg) to 90° C. whereupon the vacuum is then increased to 50 mm Hg for 0.25 hour. The vacuum is then returned to 480 mm Hg and the temperature is increased to 130° C. Additional ethylene glycol (30 g, 0.48 mole, 0.92 eq) is added dropwise over 0.2 hour then $CO_2$ is then added via a dip tube under a slight negative pressure at 1.0 g/minute or less until 68 g (1.53 mole, 2.6 eq) are added. Upon completion of $CO_2$ addition, the dip tube is removed and the temperature is increased to 200° C. under 50 mm Hg vacuum to remove solvents. The residue is vacuum filtered through a 12 mm diatomaceous earth pad in a sintered funnel yielding 489 g filtrate, a viscous brown liquid.

EXAMPLES 8-10 indicated below were prepared following the procedure of Example 7:

Example 8—calcium overbased salt of Example 2 containing 10.6% Ca,
Example 9—calcium overbased salt of Example 3 containing 8.2% Ca, and
Example 10—calcium overbased salt of Example 4 containing 8.8% Ca.

EXAMPLE 11

The procedure of Example 7 is repeated except the first heat up temperature is 95° C. and employing 100.0 g (0.04 mole, 1 eq) of the product of Example 5, 21 g (0.07 mole, 1.69 eq) stearic acid, 13.3 g (0.21 mole, 5.07 eq) ethylene glycol in the first charge, 23 g (0.37 mole, 8.93 eq) ethylene glycol in the second charge, 28.1 g (038 mole, 9.50 eq) Ca(OH)$_2$, 14.2 g mineral oil (SN150), 81 g 2-ethylhexanol solvent and 27 g (0.61 mole, 15.25 eq) $CO_2$ to yield 165 g filtrate containing 8.83% Ca and having TBN=240.2 and 100° C. viscosity=1435 cSt.

EXAMPLE 12

A 2 liter flask is charged with 276 g (0.348 mole, 1 eq) of the product of Example 4 which had been previously stripped to remove toluene, 2.8 g (0.045 mole, 0.13 eq) ethylene glycol, 16.9 g (0.229 mole, 0.66 eq) Ca(OH)$_2$, 276 g mineral oil (SN150) and 45 g 2-ethylhexanol solvent. The materials are heated, with stirring, to 90° C. at 63 kPa. Once at 90° C. the pressure is lowered to 17 kPa and is maintained for 0.5 hour. The pressure is then returned to 63 kPa and the temperature is increased to 130° C. where it is held for 0.3 hours. The temperature is increased to 200° C. and full vacuum is applied for 0.75 hour, the vacuum is then released, the residue is allowed to cool to 100° C. then is filtered. The filtrate is 560 g, 98.4% yield. % Ca=1.3, TBN=39.2 and 100° C. viscosity=99.6 cSt.

EXAMPLES 13-14 as indicated below were prepared following the procedure of Example 7:

Example 13—calcium overbased salt of Example 5 having TBN of 141, and
Example 14—borated calcium overbased salt of Example 5 having TBN of 152 and 0.4% B.

EXAMPLE 15

A reactor is charged with 12,960 g (8.95 moles) of the product of Example 6, 2333 g (31.5 moles) Ca(OH)$_2$ and 450 g ethylene glycol. While stirring, 7380 g 2-ethylhexanol are added over 0.3 hour. The materials are heated to 95° C. with −0.2 bar vacuum (~80 kPa pressure) over 0.5 hour followed by 0.8 hour at −0.56 bar vacuum (~44 kPa pressure). After 0.75 hour, 0.2 L aqueous distillate is collected. The vacuum is returned to −0.2 bar, the materials are heated to 130° C. over 0.25 hour; total aqueous distillate =0.5 L. An additional 2160 g ethylene glycol are added over 0.25 hour as the temperature drops to 125° C. The temperature is returned to 130° C. over 0.1 hour whereupon carbonation is begun at a rate of 0.5 kg/hour until a total of 750 g $CO_2$ are added. Part way through the carbonation, a sample shows the presence of water; whereupon the vacuum is reduced to −0.1 bar (~90 kPa pressure). The temperature is increased to 200° C. over 0.7 hour while vacuum is slowly applied to −0.56 bar. A total of about 5 L aqueous distillate are collected. The reaction is cooled to 80° C. and collected. Yield=22.6 kg, 97% yield. % Ca=5.1; TBN=151 mg KOHlg. $SO_4$ ash=18%.

EXAMPLE 16

The apparatus used in Example 1 is used, except the 2 litre flask is replaced with a 5 litre flask. The flask is charged with 1415 g polyisobutenyl ($\overline{M}_n$ 550, derived from GLISSOPAL® 550 (BASF)) substituted phenol (2.2 moles, 1 eq), 576 g dodecylphenol (propylene tetramer derived, 2.2 moles, 1 equivalent (eq)); and 904 g mineral oil (SN150) and heated to 30° C. Via a pressure equalizing dropping funnel, 9.9 g of 50% aqueous KOH (0.09 mole, 0.04 eq) are added all at once. The materials are heated to 75° C. followed by addition over 0.5 hour via a pressure equalizing dropping funnel, 243.6 g 37% aqueous formaldehyde (formalin) (3.0 moles, 1.36 eq) followed by heating at 75° C. for 2 hours until free formaldehyde measures less than 2% (by titration). To the reaction are charged 304 g salicylic acid (2.20 mole, 1.0 eq) and the reaction is heated to 140° C. as quickly as possible (0.3 hour) while controlling reflux, draining water of reaction via a Dean Stark trap. The reaction is held at 140° C. for 1.5 hours while collecting 267 ml water. The materials are vacuum stripped at 140° C./100 mm Hg over 0.5 hour. The clear and golden residue is the product. Yield=3165 g, % K=0.087%. Mass spec, GPC and $H^1$ and $C^{13}$ NMR indicate that the product consists of 2 methylene bridged substituted phenol molecules methylene bridged to one salicylic acid.

EXAMPLES 17-19 as indicated below were prepared following the procedure of Example 16:

Example 17—1 equiv polyisobutyl (550 molecular wt) phenol, 1 equiv $C_{12}$ phenol and 0.7 equiv of salicylic acid are coupled, Example 18—1 equiv polyisobutyl (550 molecular wt) phenol, 2.5 equiv $C_{12}$ phenol and 1 equiv salicylic acid are coupled, and Example 19—1 equiv polyisobutyl (550 molecular wt) phenol, 7.5 equiv $C_{12}$ phenol and 2.1 equiv salicylic acid are coupled.

EXAMPLE 20

A 2-liter flask is charged with 1200 g (1.06 moles, 1 eq) of Example 17. 25 g (0.4 mole, 0.38 eq) ethylene glycol, 130 g (1.75 mole, 1.65 eq) $Ca(OH)_2$, and 410 g 2-ethylhexanol (solvent). The materials are heated and stirred under vacuum (480 mm Hg) to 90° C. whereupon the vacuum is increased to 50 mm Hg for 0.25 hour. The vacuum is then returned to 480 mm Hg and the temperature is increased to 130° C. Additional ethylene glycol (120 g, 1.93 mole, 1.82 eq) is added dropwise over 0.2 hour then $CO_2$ is then added via a dip tube under a slight negative pressure at 1.0 g/minute or less until 48 g (1.2 mole, 1.13 eq) are added. Upon completion of $CO_2$ addition, the dip tube is removed and the temperature is increased to 200° C. under 50 mm Hg vacuum to remove solvents. The residue is vacuum filtered through a 12 mm diatomaceous earth pad in a sintered funnel yielding 1346 g filtrate, a viscous brown liquid.

% Ca=5.24; TBN=156 mg KOH/g; $SO_4$ ash=17.3%.

EXAMPLES 21-23 indicated below were prepared following the procedure of Example 20:

Example 21—calcium overbased metal salt of Example 18 having TBN of 145,

Example 22—calcium overbased metal salt of Example 19 having TBN of 151, and

Example 23—calcium overbased metal salt of Example 16 having TBN of 183.

Asphaltene Dispersancy

The following test assesses the level of asphaltene dispersancy provided by various phenol-salicylic acid compositions. This test relates to the problem arising from contamination of a lubricating oil with heavy fuel oil which contains residual oil to include asphaltenes.

A blend of 14.5 parts by weight of heavy fuel oil containing 10% by weight asphaltene is blended with 85.5 parts by weight Esso 150SN base oil. Each test sample is prepared by mixing, at 60° C., 8 g of this mixture with 2 g of the component to be tested, to prepare a homogenized mixture.

Whatman® brand extra thick chromatography paper (grade ET31) are prepared by marking each strip at 7.6 mm (immersion line), 13 mm above this line (spotting line) and at 15.2 cm above the spotting line (stopping line). A sample (15 µl) of each homogenized mixture is placed via micro pipette on test strips, each test strip is suspended in a 25.4 cm×2.5 cm test tube containing pentane such that the test strip is immersed in pentane up to the immersion line. The test tubes are sealed, the 15 µl spot is allowed to elute until it reached the stopping line, then the strips are removed from the tubes and allowed to dry at room temperature before rating.

Each test sample is compared with a base line, a commercially available overbased calcium salicylate anti-black paint detergent. The ability of the sample to disperse asphaltene is shown by a brown streak on the chromatogram; the better the asphaltene dispersancy (and by inference anti-black paint activity), the higher the streak length and the lower the spot intensity of the spot on the spotting line.

In the two tables below the chromatogram results show embodiments of the present invention, Examples 8-11 and 20-23, to be about comparable or superior to a commercial calcium overbased salicylate base line SAP0001 available from Infineum.

| Example number | Product description | Streak length | Spot intensity |
|---|---|---|---|
| 7 | 2:1 dodecylphenol:salicylic acid @ 300TBN | 1 | 9 |
| 8 | 1:1 Octadecylphenol:salicylic acid @ 300TBN | 2.5 | 6 |
| 9 | 2:1 Octadecylphenol:salicylic acid @ 240TBN | 2 | 2 |

-continued

| Example number | Product description | Streak length | Spot intensity |
|---|---|---|---|
| 10 | 1:1 550 PIB phenol:salicylic acid @ 250TBN | 6 | 2 |
| 11 | 2:1 550 PIB phenol:salicylic acid @ 240TBN | 5 | 2 |
| Base line, SAP001 | Commercial salicylate | 5 | 2 |
| 20 | Overbased product of Example 17 | 8 | 1 |
| 21 | Overbased product of Example 18 | 7.0 | 1 |
| 22 | Overbased product of example 19 | 8 | 1 |
| 23 | Overbased product of Example 16 | 10 | 1 |
| Base line, SAP001 | Commercial salicylate | 5 | 2 |

Panel Coker Test

The panel coker test is a standard industry bench oxidation test. A weighed aluminum plate is fixed into the side of a bath and is heated to 325° C. Test oil in the bath is periodically splashed onto the panel then it is allowed to bake between splash periods. After test, the plate is removed from the bath, washed with naphtha and is then weighed, comparing the after test weight to the starting weight. The difference is the deposit weight; the lower the deposit weight, the better the antioxidancy of the oil.

Three marine diesel lubricating oil compositions are evaluated using the panel coker test.

Lubricant 1 is a fully formulated lubricant containing ashless succinimide dispersant, mixed zinc dithiophosphate and 12.3% by weight of the product of Example 11.

Lubricant 2 is identical to lubricant 1 except the product of Example 11 is replaced with an equivalent amount of a commercially available, 280 TBN Ca salicylate.

Lubricant 3 is a commercially available Marine Diesel lubricant containing a salicylate detergent.

Test results are as follows:

| Lubricant | Deposit weight (mg) |
|---|---|
| 1 | 79 |
| 2 | 251.5 |
| 3 | 139.1 |

The antioxidancy of the lubricant containing a product of this invention is clearly superior to an otherwise identical lubricant containing a commercially available detergent and a commercially available marine diesel lubricant.

Engine Oil Oxidation Test

The engine oil oxidation test is a bench test that rates the oxidation resistance of crankcase engine oils. The test oil is placed in a flat bottomed test tube equipped with a water condenser and centrally inserted gas delivery tube. The oil sample is maintained at 170° C. with air blowing. Samples are taken at 7, 10, 12 and 14 days (end of test).

The total acid number (TAN) is measured at each sampling. TAN measures the acidity of the oil. The greater the TAN increase, the more acidic decomposition products are being produced and the more the oil is being oxidized. The slower the increase in TAN, the greater the oxidation resistance of the composition.

Each of the test samples is fully formulated partial synthetic 10W-30 lubricant containing an ashless dispersant, zinc dithiophosphate and other additives conventionally used in crankcase oils.

| Test Sample | Treatment Level | | | | | | | |
|---|---|---|---|---|---|---|---|---|
| Commercial 185 TBN Ca Salicylate | | | | | | 6 | | 3.21 |
| Commercial 65 TBN Ca Salicylate | | | | | | | | 5.5 |
| Commercial 285 TBN Ca Salicylate | | 3.07 | | | | | | |
| Commercial 250 TBN Sulfurized Ca Phenate | 3.26 | | 1.75 | | | | | |
| Commercial 150 TBN Sulfurized Ca Phenate | | | | 2.76 | | | 5.73 | |
| Example 11 (240 TBN) | | | | 2.1 | | | 5.26 | |
| Example 9 (239 TBN) | | 3.47 | | 3 | | | 2.64 | |
| TAN increase @ 7 days | 6.32 | 3.85 | 3.88 | 6.5 | 4.36 | 3.91 | 9.09 | 3.76 | 3.23 |
| TAN increase @ 10 days | 8.95 | * | 5.94 | 9.26 | 5.79 | 5.72 | 12.5 | 5.49 | 4.85 |
| Tan increase @ 12 days | 10.22 | 7.05 | 7.49 | 10.5 | 6.35 | 6.63 | 13.99 | 6.65 | 6.32 |
| TAN increase @ 14 days (End of Test) | 11.49 | 7.05 | 8.19 | 11.77 | 8.85 | 9.38 | 14.11 | 7.21 | 6.79 |

*Result invalid

It can be seen from the data above that Examples 9 and 11 slow the TAN increase considerably (i.e. are good antioxidants) in comparison to phenates and compare well against salicylates, especially when compared on an equal substrate level basis.

High Frequency Reciprocating Rig (HFRR)

The HFRR test is a standard industry test for wear. The test employs apparatus as described in ASTM D-6079.

Testing is conducted with blends containing 5% by weight of the specified component in SN150 mineral oil base. The result is given in 2 forms, first as a wear scar diameter in microns and then this figure standardized to take into account atmospheric pressure, humidity and temperature (the WS14 result). The lower the wear scar diameter and WS14 figure the better. <400μ is considered a pass. Test results are Product of Example 13: WS 14 258 μm, scar average 268 μm.

Product of Example 14: WS 14 225 μm, scar average 208 μm

Both compounds pass the test. However, the boron-containing product provides superior antiwear performance.

TDI and T4 Engine Tests

These are severe passenger car motor oil (PCMO) engine tests which must be passed to meet European top tier engine oil specifications. In these tests a matrix of 6 packages were run, 3 at 1.0% ash, 3 at 1.4% ash. The 3 packages of the same ash had the TBN provided either by a standard phenate/sulphonate mix, the 150TBN overbased salt of Example 15 or 165TBN salicylate ex Infineum. The packages were otherwise typical top tier European PCMO 5W-30 packages and contained identical amounts and types of PIB succinimide dispersants, zinc dialkyl thiophosphate antiwear agents, antioxidants and viscosity modifiers.

First the TDI results. These were run as a "no harm" test, and it can be seen that within the bounce of the test all the packages are similar, showing the Example 15 type material is not harmful to the engine and is comparable in performance to standard salicylates or phenate/sulphonate.

|  | Invention Package | Package 2 | Poor reference* | Good reference | E4 limits |
|---|---|---|---|---|---|
| Piston Merit | 41.5 | 43.3 | 25.9 | 46.6 | 40 |
| Bore Polish % | 0.5 | 1.9 | 0.23 | 1.06 | 2 |
| Oil consumption kg | 25.3 | 36.6 | 25.2 | 32.5 | 40 |

*Average of 2 runs

The above table shows some recent OM441LA test runs. Package 2 is a commercial multigrade high performance ACEA E4 (the latest European Top-Tier HD specification) passing formulation. In the Invention Package (referred to in the above table) 45% of the overbased detergent substrate in package 2 is replaced with the 150TBN product of Example 15. All the other package ingredients (PIB succinimide dispersants, zinc dialkyl thiophosphate antiwear agents, antioxidants and viscosity modifiers) remain the same for both packages. It can be seen that substitution of Example 15 gave similar piston merit and significantly lowered oil consumption and bore polish. The results of two standard reference oils (a "good" and a "bad") are also given for comparison.

Engine Oil Bench Tests

A standard Top Tier Heavy Duty Diesel package ("sulf/phen" in table below) was run in a series of bench tests. It was The TDI results are represented in tabular form.

| TDI Criteria | Phenate/Sulph 1% Ash | Salicylate 1% Ash | Example 15 1% Ash | Phenate/Sulph 1.4% Ash | Salicylate 1.4% Ash | Example 15 1.4% Ash |
|---|---|---|---|---|---|---|
| Merit (66 min) | 59 | 61 | 59 | 68 | 68 | 66 |
| Ring Stick (0.7 max) | 0.13 | 0 | 0.44 | 0 | 0 | 0 |

The T4 data is also represented in tabular form below.

| T4 Criteria | Phenate/Sulph 1% Ash | Salicylate 1% Ash | Example 15 1% Ash | Phenate/Sulph 1.4% Ash | Salicylate 1.4% Ash | Example 15 1.4% Ash |
|---|---|---|---|---|---|---|
| Merit (1 min) | 2.22 | 1.69 | 2.94 | 3.62 | 4.52 | 5.14 |
| % Vis increase (130 max) | 116.1 | 211.2 | 170.7 | 201.9 | 107.7 | 148.0 |
| EOT vis, CSt (200 max) | 139.5 | 199.3 | 182.5 | 201.6 | 139.9 | 173.7 |

At high ash the package containing Example 15 is overall better than phenate/sulphonate and at low ash is overall better than salicylate. At all ash levels Example 15 has better merit than either phenate/sulphonate or salicylate.

OM441LA Test

This is a severe heavy duty diesel test in Europe, which is very difficult to pass with conventional materials.

then compared against the same package where all the overbased detergents (phenates and sulphonates) were replaced with: the 150TBN 550 Mn PIB phenol detergent of Example 15 ("550 PIB" in the table below); the boronated 550 Mn PIB phenol detergent of Example 14 ("Borated 550 Pib" in the table below): and the dodecyl phenol detergent of Example 7 ("$C_{12}$" in the table below). All the other package ingredients (PIB succinimide dispersants, zinc dialkyl thiophosphate antiwear agents, antioxidants and viscosity modifiers) remained the same for all the packages.

|  | Sulf/Phen | 550 PIB | Borated 550 PIB | $C_{12}$ |
|---|---|---|---|---|
| PDSC | 56.6 | 57.8 | 58.4 | 50.6 |
| VW seals tensile | 52.2 | 47.1 | 44 | 54.8 |
| VW elong | 37.7 | 39.6 | 44.7 | 46.6 |
| Severe VW tensile | 8.2 | 7.2 | 9.3 | 6.9 |
| Severe VW elongation | 192 | 179.3 | 204.5 | 170.1 |
| Oxid/nitration C=O Increase | −31.23 | −16.65 | −11.92 | 29.02 |
| Oxid/nitration RONO2 | 17 | 15.1 | 18.3 | 22.3 |
| GF-2 TEOST | 54.8 | 39.3 | 38.1 | 46.9 |

The first test (PDSC) is the Pressure Differential Scanning Calorimeter test, a standard bench test in the lubricating oil industry (CEC L-85 T-99). In this test, the oil is heated to an elevated temperature and the time to when the oil begins to decompose measured. The longer this time, the better. It can be seen that the 550 Mn PIB-based detergent of Example 15 ("550 PIB" in table above) and the borated detergent of Example 14 are slightly better than the sulf/phen base line, but the dodecyl detergent of Example 7 is much worse. This is another example to show that the alkyl chain length in the inventive detergents is preferably $C_{18}$ or greater.

The next four rows concern a seal swell test using Volkswagen engine seals. In the standard test in rows 2 and 3 the lower the number the better. In this standard test it can be seen that $C_{12}$ detergent of Example 7 performs worse than the 550 PIB detergent of Example 15 or its borated derivative of Example 14. In the severe test in rows 4 and 5, the higher the number the better. Here the $C_{12}$ detergent of Example 7 is again the worst performer, the 550 PIB detergent of Example 15 shows no harm w.r.t the standard package, but its boronated derivative of Example 14 is better than the standard. This is another example to show that the alkyl chain length in inventive compounds is preferably $C_{18}$ or greater, and an example to show the benefit of boronation.

Rows 6 and 7 are an oxidation test where the sample is purged with NOx for 22 hours at 145° C. and the C=O region and R—O—NO2 region monitored before and after the test by FTIR. An increase in these regions is bad. In this standard test it can be seen that the $C_{12}$ detergent of Example 7 performs worse than the than 550 Mn PIB detergent of Example 15 and its boronated derivative of Example 14. This is another example to show that the alkyl chain length in the inventive compounds is preferably $C_{18}$ or greater.

Row 8 is the TEOST test. In this a steel rod is cycled in the sample from 200-480° C. and the amount of deposits formed on the rod and in the oil are measured. The lower the deposits the better. In this test all the examples perform better than the standard, but the $C_{12}$ detergent of Example 7 performs least well of the inventive examples. This is another example to show that the alkyl chain length in the inventive compounds is preferably $C_{18}$ or greater.

It is known that some of the materials described above may interact in the final formulation, so that the components of the final formulation may be different from those that are initially added. For instance, metal ions (of, e.g., a detergent) can migrate to other acidic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

Each of the documents referred to above is incorporated herein by reference. Except in the examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain isomers, by-products, derivatives, and other such materials which are normally understood to be present in the commercial grade. However, the amount of each chemical component is presented exclusive of any solvent or diluent oil which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. A linear compound comprising m units of formula (I)

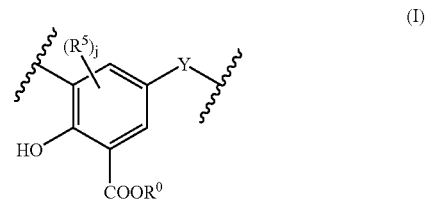

and n units of the formula (II)

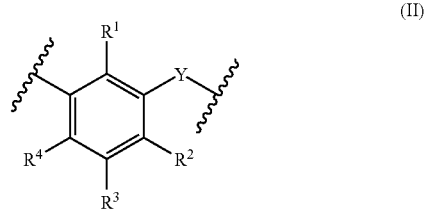

joined together, each end of the compound having a terminal unit which is independently hydrogen or one of the following formulae:

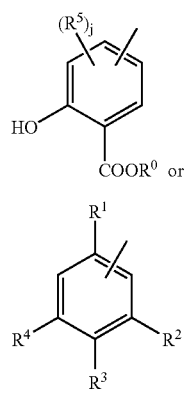

(III)

(IV)

wherein at least one of the terminal units is formula (III) or (IV); Y is a divalent bridging group which may be the same or different in each unit and that joins together the units of formulae (I)-(IV) and is $(CHR^6)_d$ in which $R^6$ is hydrogen and d is an integer which is at least 1; $R^0$ is hydrogen; $R^5$ is hydrogen or a hydrocarbyl group; j is 1 or 2; $R^3$ is a hydrocarbyl or a hetero-substituted hydrocarbyl group, where $R^3$ contains 1 to 100 carbon atoms; $R^1$ is hydroxyl and $R^2$ and $R^4$ are independently either hydrogen, hydrocarbyl or hetero-substituted hydrocarbyl, provided that at least one of $R^1$, $R^2$, $R^3$ and $R^4$ is hydrocarbyl containing on average at least 18 carbon atoms; wherein m is at least 1 and n is at least 2,; wherein on average the compound contains at least one unit of formula (I) or (III) and at least one unit of formula (II) or (IV); and the compound has a ratio of total number of units of formulae (I) and (III) to total number of units of formulae (II) and (IV) of about 0.1:1 to about 2:1; and the compound is either an alkali or an alkaline earth metal salt having a TBN of 60 to 500 mg KOH/g.

2. The linear compound of claim 1 containing at least one block containing at least two units corresponding to formula (II) attached to each other.

3. The compound of claim 1 wherein m+n is about 3 to about 50.

4. The compound of claim 1 wherein $R^0$ is hydrogen; $R^1$ is hydroxyl; $R^2$ and $R^4$ are hydrogen; $R^3$ is a hydrocarbyl group, $R^5$ and $R^6$ are hydrogen, and d is 1.

5. The composition of claim 1 wherein the compound contains one or more units of formulae (II) and (IV) wherein a portion of said units have a $R^3$ hydrocarbyl group containing about 8 to about 20 carbon atoms and the remaining portion of said units have a $R^3$ hydrocarbyl group containing about 21 to about 45 carbon atoms.

6. The composition of claim 1 wherein the metal salt of the compound contains boron.

7. A concentrate comprising the compound of claim 1 and an organic diluent, the concentration of the organic diluent ranging from about 1 to about 99% by weight.

8. A lubricating oil composition, comprising a minor amount of the compound of claim 1 and a major amount of a lubricating oil.

9. The lubricating oil composition of claim 8 wherein the lubricating oil composition further comprises a contaminate amount of fuel oil having a residual oil content.

10. A process for making a linear compound metal salt comprising the steps:

step (I) preparing the linear compound by reacting together, optionally in an organic solvent, and in the presence of a basic catalyst, compounds of the formulas (Ia) and (IIa)

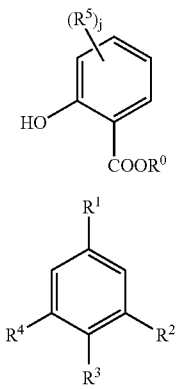

(Ia)

(IIa)

with an aldehyde; wherein $R^0$ is hydrogen or a hydrocarbyl group; $R^5$ is hydrogen or a hydrocarbyl group; j is 1 or 2; $R^3$ is a hydrocarbyl or a hetero-substituted hydrocarbyl group, where $R^3$ contains 1 to 100 carbon atoms; $R^1$ is hydroxyl and $R^2$ and $R^4$ are independently either hydrogen, hydrocarbyl or hetero-substituted hydrocarbyl, provided that at least one of $R^1$, $R^2$, $R^3$ and $R^4$ is hydrocarbyl containing on average at least 18 carbon atoms; the number of molar units of the compound represented by formula (Ia) being m, the number of molar units of the compound represented by formula (IIa) being n, wherein m is at least 1 and n is at least 2, and the ratio of m to n ranging from about 0.1:1 to about 2:1;

step (II) forming a mixture of components (A) and (C); component (A) being the compound prepared in step (I); component (C) being a solvent comprising either component (C-1) or (C-2); component (C-1) being either (i) a polyhydric alcohol having 2 to 4 carbon atoms; (ii) a di-($C_3$ or $C_4$) glycol, (iii) a tri-($C_2$-$C_4$) glycol or (iv) a mono- or poly-alkylene glycol alkyl ether of the formula:

$$R^1(OR^2)_fOR^3 \qquad (V)$$

wherein the formula (V), $R^1$ is an alkyl group of 1 to about 6 carbon atoms, $R^2$ is an alkylene group of 1 to about 6 carbon atoms, $R^3$ is hydrogen or an alkyl group of 1 to about 8 carbon atoms, and f is an integer from 1 to about 6; component (C-2) being a monohydric alcohol of 1 to about 4 carbon atoms in combination with a hydrocarbon solvent; and step (III) adding a metal base (B) to the mixture of components (A) and (C), the addition of the metal base (B) to the mixture of (A) and (C) being in a single addition or in a plurality of additions, steps (II) and (III) being performed concurrently or sequentially.

11. The process of claim 10 including an initial oli-gomerization step in step (I) wherein the compound corresponding to formula (IIa) is permitted to react prior to the addition of the compound corresponding to formula (Ia).

12. The process of claim 10 wherein to basic catalyst is alkali or alkaline earth metal hydroxide, ammonia, a hindered amine or a basic ion exchange resin.

13. The process of claim 10 with the additional step of:

Step (IV) adding (D) carbon dioxide to the mixture of components (A), (B) and (C) subsequent to each addition of component (B).

14. The process of claim 13 wherein during step (I), (II), (III) or (IV), or prior to or subsequent to step (I), (II), (III) or (IV), the reaction mixture further comprises component (E); component (B) being either (i) a carboxylic acid or anhydride thereof containing about 6 to about 100 carbon atoms; (ii) a di- or polycarboxylic acid or anhydride thereof containing from about 36 to about 100 carbon atoms; (iii) a hydrocarbyl-substituted sulphonic acid or anhydride thereof; (iv) a hydrocarbyl-substituted salicylic acid or anhydride thereof; (v) a hydrocarbyl-substituted naphthenic acid or anhydride thereof; (vi) a hydrocarbyl-substituted phenol; or (vii) a mixture of two or more of (i) to (vi).

15. The process of claim 10 wherein the mole equivalent ratio of component (B) to component (A) is from about 0.05 to about 20 mole equivalents of (B) per mole equivalent of (A).

* * * * *